(12) United States Patent
Parsons

(10) Patent No.: US 6,558,348 B2
(45) Date of Patent: May 6, 2003

(54) LOW COST DISPOSABLE NEEDLELESS INJECTOR SYSTEM FOR VARIABLE AND FIXED DOSE APPLICATIONS

(75) Inventor: J. Stuart Parsons, Aliso Viejo, CA (US)

(73) Assignee: Equidyne Systems, Inc., San Diego, CA (US)

( * ) Notice: Subject to any disclaimer, the term of this patent is extended or adjusted under 35 U.S.C. 154(b) by 0 days.

(21) Appl. No.: 09/751,525

(22) Filed: Dec. 29, 2000

(65) Prior Publication Data

US 2001/0051789 A1 Dec. 13, 2001

Related U.S. Application Data

(60) Provisional application No. 60/195,389, filed on Apr. 7, 2000.

(51) Int. Cl.$^7$ ............................... A61M 5/30
(52) U.S. Cl. ............................................ 604/68
(58) Field of Search ........................... 604/68–73, 134, 604/135

(56) References Cited

U.S. PATENT DOCUMENTS

| | | | |
|---|---|---|---|
| 2,800,903 A | | 7/1957 | Smoot |
| 3,828,775 A | * | 8/1974 | Armel ........................ 128/218 |
| 4,015,709 A | * | 4/1977 | Millet ........................ 206/366 |
| 4,094,195 A | * | 6/1978 | Friswell et al. ............... 73/422 |
| 4,103,684 A | * | 8/1978 | Ismach ....................... 128/173 |
| 4,266,541 A | * | 5/1981 | Landau ..................... 128/207.23 |
| 4,680,027 A | | 7/1987 | Parsons et al. ................ 604/68 |
| 4,722,728 A | * | 2/1988 | Dixon ......................... 604/68 |
| 4,874,367 A | | 10/1989 | Edwards ...................... 604/72 |
| 4,913,699 A | * | 4/1990 | Parsons ....................... 604/68 |
| 5,024,656 A | | 6/1991 | Gasaway et al. ............... 604/68 |
| 5,062,833 A | * | 11/1991 | Perler ........................ 604/110 |
| 5,320,616 A | * | 6/1994 | Magruder et al. ........... 604/892.1 |
| 5,334,144 A | * | 8/1994 | Alchas et al. .................. 604/68 |
| 5,344,395 A | * | 9/1994 | Whalen et al. ................. 604/22 |
| 5,499,972 A | | 3/1996 | Parsons ....................... 604/70 |
| 5,549,558 A | * | 8/1996 | Martin ........................ 604/110 |
| 5,569,189 A | | 10/1996 | Parsons ....................... 604/68 |
| 5,704,911 A | | 1/1998 | Parsons ....................... 604/72 |
| 5,733,261 A | * | 3/1998 | Obong ........................ 604/110 |
| 5,788,677 A | * | 8/1998 | Botich et al. ................. 604/195 |
| 6,102,896 A | | 8/2000 | Roser ......................... 604/218 |
| 6,135,979 A | | 10/2000 | Weston ........................ 604/68 |

FOREIGN PATENT DOCUMENTS

| WO | WO 00/48654 | 8/2000 |
|---|---|---|
| WO | WO 00/50107 | 8/2000 |
| WO | WO 00/53160 | 9/2000 |

* cited by examiner

*Primary Examiner*—Anhtuan T. Nguyen
*Assistant Examiner*—Ann Y. Lam
(74) *Attorney, Agent, or Firm*—Christie, Paker & Hale, LLP

(57) ABSTRACT

A disposable needleless injection device includes an integral unit that is dimensioned and arranged to be grasped in the hand of a user. The system is spring-loaded and is manufactured and shipped with the spring in a pre-cocked condition. An integral ampule is fillable by manipulation of a thrust rod/shaft which extends longitudinally through the device and is able to be grasped by a user. Once the unit is filled with a selected medication, it is held proximate the skin in order to inject the selected dosage. The unit is constructed from a maximum of eight component parts and is assembled in a matter of moments by unskilled personnel.

66 Claims, 9 Drawing Sheets

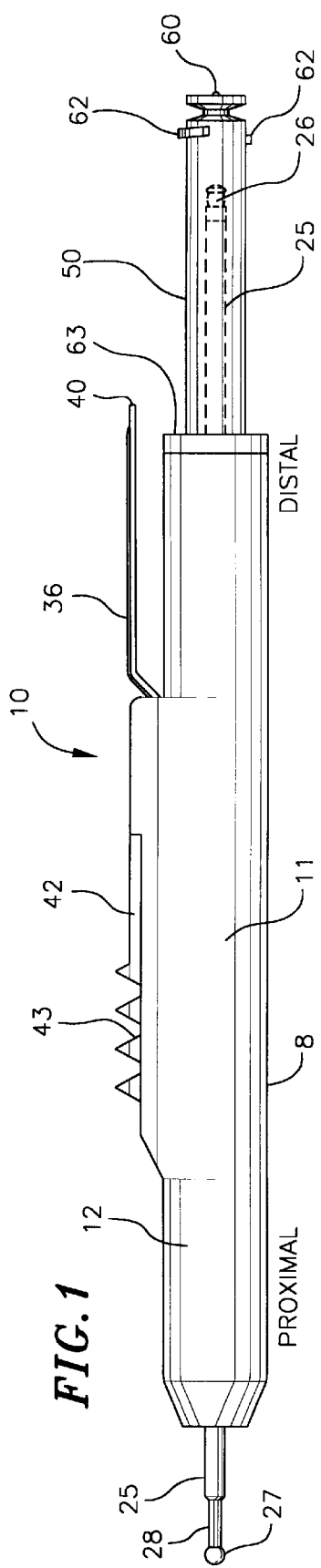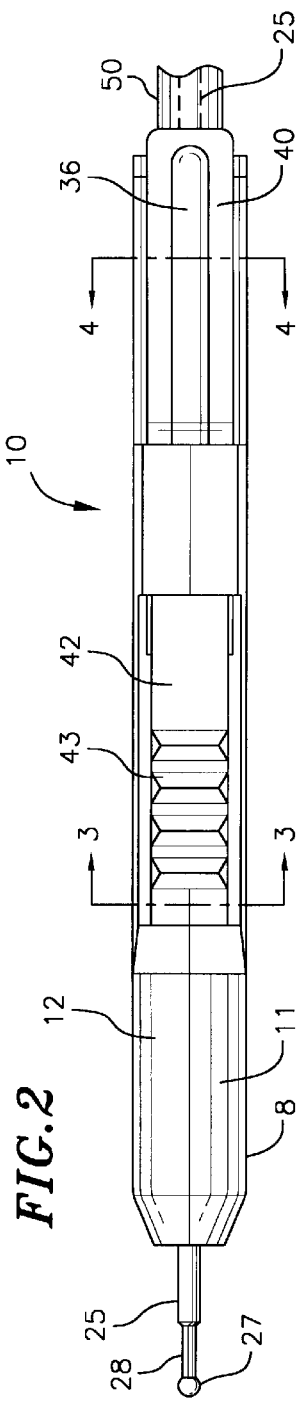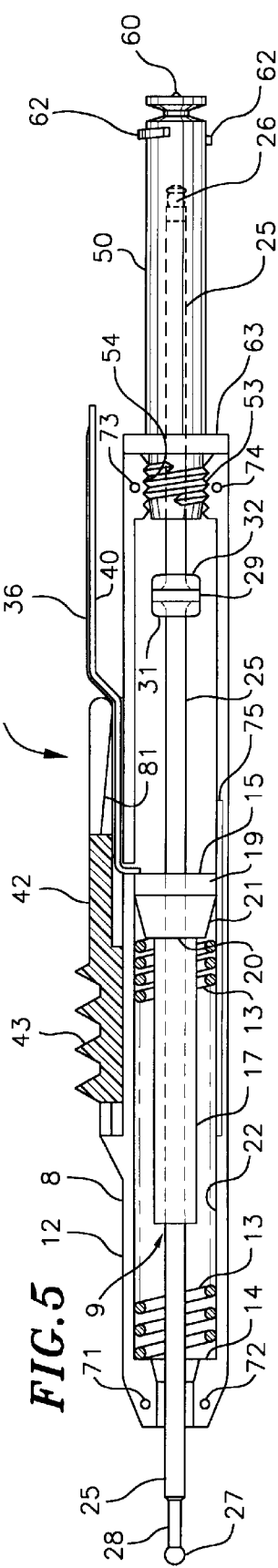

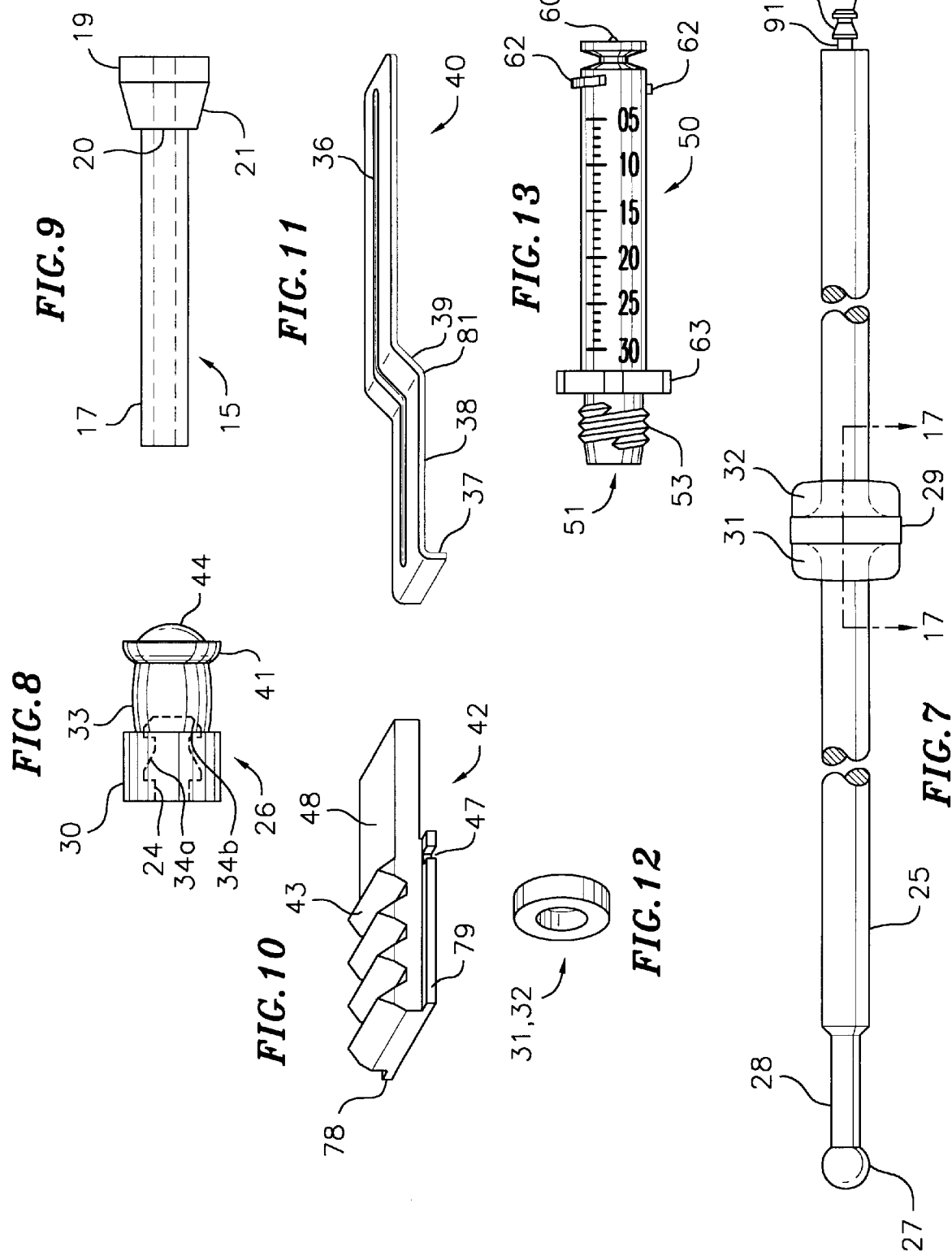

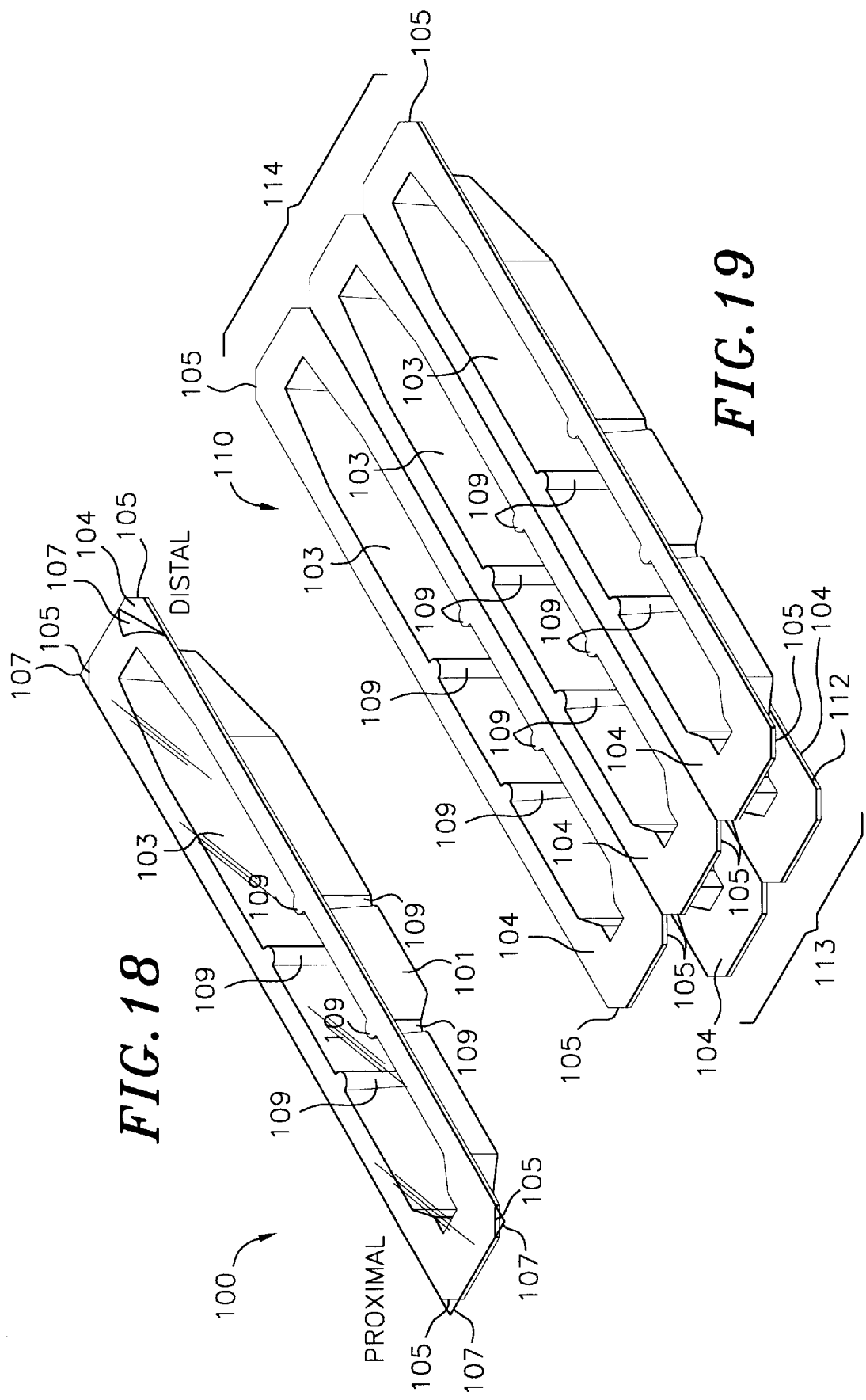

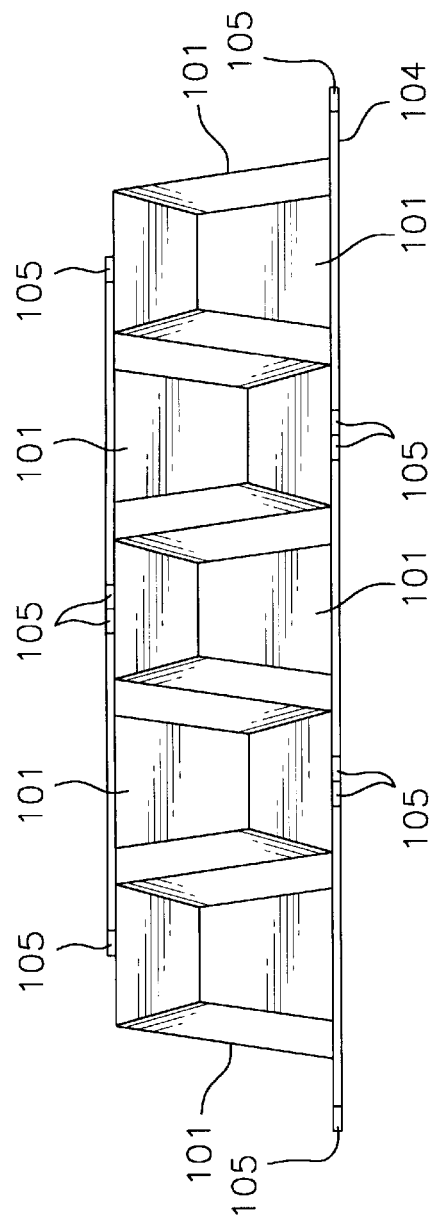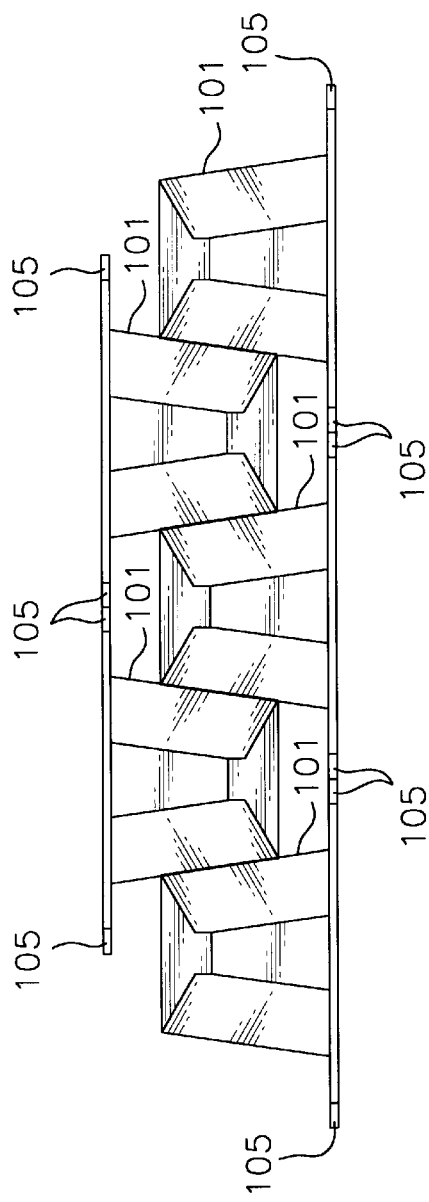

LOW COST DISPOSABLE NEEDLELESS INJECTOR SYSTEM FOR VARIABLE AND FIXED DOSE APPLICATIONS

PRIORITY CLAIM

This patent application claims the benefit of the filing date of U.S. provisional patent Application No. 60/195,389, filed on Apr. 7, 2000, entitled LOW COST DISPOSABLE NEEDLELESS INJECTOR SYSTEM FOR VARIABLE AND FIXED DOSE APPLICATIONS, the entire contents of which is hereby expressly incorporated by reference.

FIELD OF THE INVENTION

The present invention relates generally to needleless hypodermic drug delivery devices and methods. The present invention relates more particularly to a low cost, disposable, spring actuated needleless injection device which utilizes a high pressure liquid stream to inject a medicament or other liquid through the skin and also relates more particularly to a method for using and manufacturing the same.

BACKGROUND OF THE INVENTION

Needleless injection devices which administer intramuscular and/or subcutaneous medications without the use of a needle are well known. Among the many advantages of such needleless injection devices are the reduction of pain and apprehension commonly associated with hypodermic needles, the elimination of needle stick injuries, and the reduction of environmental pollution associated with contaminated needle disposal. Moreover, needleless injection devices are useful in a wide range of drug therapies, including the administration of vaccines, hormone therapies and local anesthetics. Further, it is well known that such needleless injection devices are useful in the administration of insulin to the diabetic population, where individuals frequently require a number of daily injections.

Injectable medications fall into two different general categories, namely: unit dose drugs such as vaccines and analgesics; and variable dose drugs such as insulin, where the dose size must be adjusted specifically so as to meet the immediate needs of the individual at the time of administration. When a variable dose is required, as in the case of the administration of insulin, a very accurate amount of medication must be transferred to a variable dose ampule of the needleless injector. Insulin doses are typically marketed in 3 ml and 5 ml syringe cartridges, as well as being provided in bulk in a standard 10 ml medication vial.

The use of needleless injection devices has recently become of great interest, particularly by people of limited physical abilities such as the elderly, the very young and the infirm. Such persons with limited physical abilities may find the use of conventional needle syringes either difficult or impossible. Therefore, the simplified injection process associated with needleless injectors makes their use very desirable among such people.

The principles of needleless injection and the advantages of such needleless drug delivery systems over conventional hypodermic needle injection systems have long been known. However, very few needleless injection devices have achieved commercial success in the marketplace. This lack of acceptance by the user community can be attributed, at least in part, to a number of factors, chief among which are: mechanical designs which have the potential to inflict serious injury if an injector device is inadvertently fired without a medicament container or ampule in place, undesirably complex filling techniques, and the high cost of such contemporary injection devices. This cost disadvantage is particularly troublesome for those individuals who must self-administer a large number of daily injections, such as diabetics.

One existing needleless injection device is described in U.S. Pat. No. 4,874,367 to Edwards. It employs a sealed ampule that is prefilled with a selected amount of medication. The prefilled ampule is attached to a separate spring-loaded firing mechanism which, when triggered, propels a ramrod from the front of the mechanism and against a plunger located in the ampule. The ramrod drives the plunger against the medication, producing a high pressured jet for injection purposes. The plunger expels the medication from a discharge orifice and into the patient's subcutaneous tissue.

Although effective in some respects, this contemporary needleless injection device is severely limited in practical applications. In order to cock the firing mechanism, the user is required to force the ramrod back into the firing mechanism by pushing the device against a solid surface, such as a table top, until the ramrod latches behind a trigger mechanism. Thus, the strength of an individual user imposes a strict limit upon the spring force that can be utilized in the device. Many elderly, very young or infirm people simply do not have the physical strength required to cock the firing mechanism of such a contemporary needleless injection device.

Moreover, employing a spring force which is low enough to be practical for the elderly, the very young and the infirm to cock the device results in the spring force being inadequate to produce effective and reliable injection pressures for most adults. That is, such a device would generally lack the ability to penetrate the skin and subcutaneous tissue sufficiently to insure proper, reliable, operation thereof.

In addition, the firing mechanism, having a spring actuated ramrod which extends outside of the device body, has the potential to inflict serious injury if inadvertently fired without the ampule in place. For example, firing such a device without having the ampule attached thereto may result in harm to a person who is inadvertently struck with the rapidly moving ramrod.

Moreover, the fixed dose ampule of contemporary needleless injection devices such as those of the '367 patent must be prefilled at the factory and then attached to the injector when required for usage. In actual practice, however, this procedure is not practical for the simple reason that drug products cannot generally be stored in plastic containers for the extended periods of time which are typically experienced by such factory prefilled ampules. The only approved material for long term liquid medication storage is type-1 glass, which is used for virtually all drug products. However, due to the dynamics of needleless injection, in which the ampule is subjected to very high pressures during the ejection process, glass is not a suitable material for the ampule because it is too easily shattered. Consequently, it is desirable to have an ampule which may be coupled to a conventional drug vial or other medication container at the time of use, and then be filled therefrom with an accurate dose of medication. The ampule should be made of a high strength plastic material.

Indeed, the needleless injection device of U.S. Pat. No. 4,874,367 is formed of durable materials and utilizes comparatively expensive manufacturing techniques, so as to assure long time reliable use thereof. As such, this device is comparatively expensive to manufacture. The expense associated with the manufacture of this device precludes the sale and use of this device as a single use, disposable needleless injector.

U.S. Pat. No. 4,913,699 to Parsons overcomes some of the aforementioned deficiencies associated with contemporary needleless injectors. This patent describes a disposable needleless injection device having a firing mechanism that operates to release compressed gas from a storage compartment. The compressed gas acts upon a piston which drives a plunger that ejects a selected dosage of medication through an aperture in the discharge end of the device. However, the medication to be administered must first be drawn into a chamber provided in the interior of the injector before being dispensed. Thus, although being pre-cocked, and loadable (with medicine), the device is rather complicated to use. In addition, no provision is made for filling the medication chamber directly from standard medication containers. In order to fill the medication chamber, a complex liquid transfer system is required.

The device disclosed in the '699 patent is relatively complex. It is manufactured from materials able to withstand the pressures associated with a compressed gas activation system. Indeed, this needleless injection device is formed of comparatively durable materials and utilizes comparatively expensive manufacturing techniques, so as to assure long term reliable operation thereof in light of the aforementioned pressures. As such, this device is comparatively expensive to manufacture. The expense associated with the manufacture of this device precludes its sale and use as a single use, disposable item.

Thus, although the aforementioned contemporary needleless injection systems are compact and reliable, they are too complex and expensive to manufacture in order to be considered disposable.

In view of the foregoing, it is clear that there is a need in the art for a needleless hypodermic injection device which has an enhanced simplicity of design and which can be manufactured from a small number of low cost components in order to be implemented as a truly disposable system. Furthermore, there is a need for a needleless hypodermic injection system which includes a medication ampule which is capable of being filled with an accurate dose of medication and which does not impose a risk of injury due to needle use and which does not contribute to the contamination hazards attendant with needle disposal.

In this regard, it is desirable to provide a convenient, low cost and disposable needleless injector device that is configured to be conveniently and comfortably grasped in one hand of a user in a manner which facilitates self-administration of a desired medication. The system should comprise a firing mechanism and an ampule cooperating in a novel design having simplicity in both structure and function. The ampule should be such that the user may fill it with a selected dosage conveniently and accurately from existing medication vials, so as to facilitate both variable and fixed dose applications. The injector firing mechanism should be conveniently and safely operated without the need for a user to force the apparatus against a piece of furniture or the like in order to cock a spring. There should be no substantial danger associated with firing the device without an ampule in place.

SUMMARY OF THE INVENTION

The present invention specifically addresses and alleviates the above-mentioned deficiencies associated with the prior art. More particularly, the present invention comprises a housing and a spring injector mechanism disposed at least partially within the housing. Preferably, the spring injector mechanism and/or the housing are configured to be used only one time.

Preferably, the needleless injector of the present invention is provided with a spring injector mechanism which is already compressed or cocked when purchased, such that the user does not have to cock the device. Thus, the needleless injector of the present invention is particularly suitable for the elderly, the very young and the infirm.

Further, the needleless injector of the present invention is preferably configured such that it is generally suitable for only a single use.

Thus, according to the present invention, a low cost, disposable needleless injector is provided, so as to facilitate the administration of injections such as vaccines, hormones, local anesthetics and insulin.

It is understood that changes in the specific structure shown and described may be made within the scope of the claims without departing from the spirit of the invention.

BRIEF DESCRIPTION OF THE DRAWINGS

These and other features, aspects and advantages of the present invention will be more fully understood when considered with respect to the following detailed description, appended claims and accompanying drawings, wherein:

FIG. 1 is a semi-schematic side view of the low cost, disposable needleless injector of the present invention, as it is provided by a supplier, i.e., cocked and having an empty ampule;

FIG. 2 is a semi-schematic top view of the needleless injector of FIG. 1;

FIG. 5 is a semi-schematic cross-sectional side view of the needleless injector of FIG. 1;

FIG. 7 is a semi-schematic side view of the shaft of FIG. 1;

FIG. 8 is a semi-schematic side view of the plunger of FIG. 1;

FIG. 9 is a semi-schematic side view of the piston of FIG. 5;

FIG. 10 is a semi-schematic perspective view of the safety slide of FIG. 1;

FIG. 11 is a semi-schematic perspective view of the trigger of FIG. 1;

FIG. 12 is a semi-schematic perspective view of an exemplary one of the two elastomeric washers or cushions of FIG. 5;

FIG. 13 is a semi-schematic side view of the ampule of FIG. 1;

FIG. 18 is a semi-schematic perspective view of a package for a single needleless injector according to the present invention;

FIG. 19 is a semi-schematic perspective view of a volume efficient cluster of packages for containing a plurality of the needleless injectors of the present invention, wherein a plurality of single needleless injector packages have been formed to one another;

FIG. 21 is a semi-schematic end view of the cluster of packages of FIGS. 19 and 20, showing the distal end thereof; and FIG. 22 is a semi-schematic end view of the cluster of packages of FIGS. 19 and 20, showing the proximal end thereof.

DETAILED DESCRIPTION OF THE INVENTION

Figure 3:
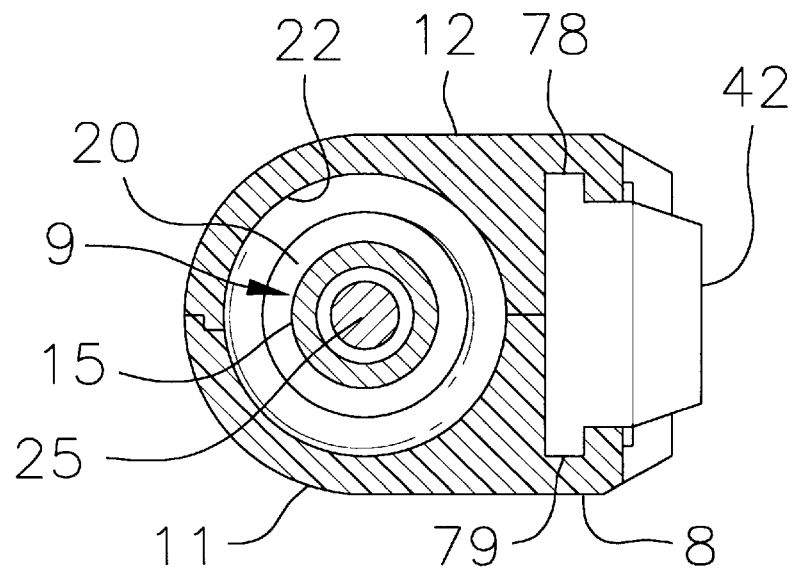
FIG. 3 is a semi-schematic cross-sectional end view of the needleless injector taken along line 3 of FIG. 2.
Figure 4:
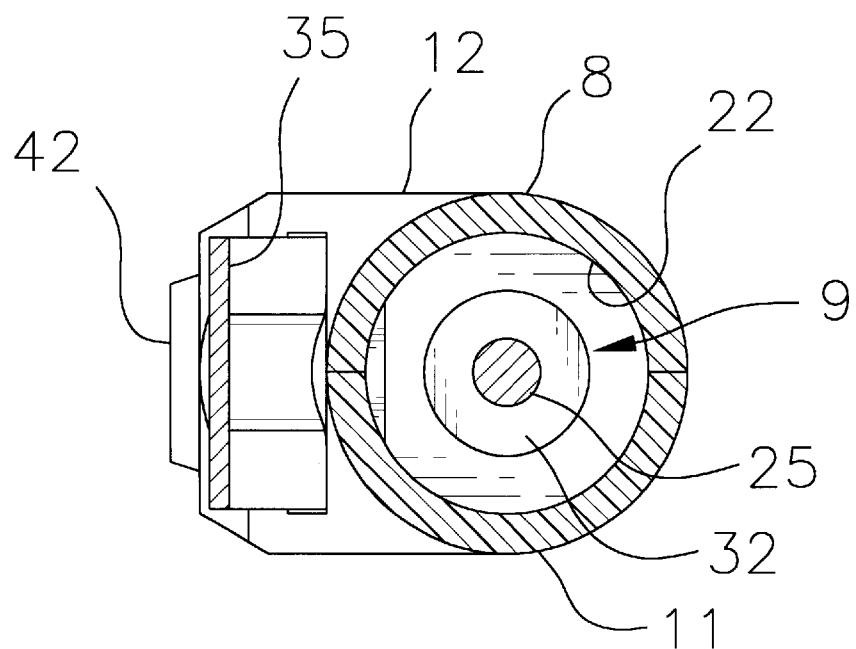
FIG. 4 is a semi-schematic cross-sectional end view of the needleless injector taken along line 4 of FIG. 2.

The detailed description set forth below in connection with the appended drawings is intended as a description of the presently preferred embodiment of the invention, and is not intended to represent the only form in which the present invention may be constructed or utilized. The description sets forth the construction and functions of the invention, as well as the sequence of steps for operating the invention in connection with the illustrated embodiment. It is to be understood, however, that the same or equivalent functions may be accomplished by different embodiments that are also intended to be encompassed within the spirit and scope of the invention.

According to the present invention, a low cost, disposable needleless injector is provided so as to facilitate the administration of drug therapies such as vaccines, hormones, local anesthetics and insulin. The disposable needleless injector of the present invention is pre-cocked at the factory, so as to eliminate any need for a user to cock the needleless injector. Thus, the disposable needleless injector of the present invention is well suited for use by the elderly, the very young and the infirm, as well as any other persons who may find cocking of such devices difficult and/or unsafe. This device is also very easy for healthcare workers and the like to use on a patient. Thus, the present invention is well suited for both the self-administration of medication and for the injection of others, such as by healthcare workers.

The needleless injector of the present invention is specifically configured so as to be suitable for only a single use. Such configuration of the present invention is accomplished, at least in part, via the selection of particular materials which provide safe and reliable operation for a single use, but which are not suitable for indefinitely repeated use thereof. Single use of the needleless injector of the present invention is further facilitated by the mechanical design thereof, which readily facilitates cocking of the device at the factory, but which substantially inhibits cocking by a user. Indeed, cocking of the present invention by a user is virtually impossible.

Further, the needleless injector of the present invention preferably has an ampule permanently attached thereto, such that repeated use is inhibited and such that any hazard associated with firing of the device with an ampule not attached thereto is substantially mitigated.

More particularly, the low cost, disposable needleless injector of the present invention comprises a housing and a spring injector mechanism disposed at least partially within the housing. The spring injector mechanism and/or the housing are configured specifically so as to be used only a single time. For example, the spring injector mechanism is configured so as to inhibit cocking thereof by a user, such as by providing a shaft which cannot easily be grasped and pulled in a manner which is necessary to effect cocking of the needleless injector. Thus, the spring injector mechanism is configured so as to require a specially designed machine tool to facilitate cocking thereof. Of course, this machine tool is not available to the general public.

Those skilled in the art will appreciate that various locks, catches, latches, detents and the like may be utilized to prevent re-cocking of the spring injector mechanism. For example, actuation of the spring injector mechanism may trip a latch which prevents further movement, i.e., re-cocking, of a shaft of the spring injector mechanism. Such a latch would be disposed within the housing, and thus not be easily disengaged by a user. In this manner, a user is substantially inhibited from re-cocking the spring injector mechanism, so as to facilitate reuse thereof. Those skilled in the art will appreciate that various other, different methods for mechanically locking at least a portion of the spring injector mechanism in the fired position, after a single use thereof, are likewise suitable for inhibiting re-use of the present invention.

As stated above, the housing and/or the spring injector mechanism are configured so as to be unsuitable for indefinitely repeated use of the present invention. This may alternatively be accomplished, for example, by utilizing materials which inhibit repeated use thereof. Thus, the needleless injector of the present invention is preferably formed of materials which are insufficiently durable so as to facilitate repeated use thereof. That is, the low cost disposable needleless injector of the present invention is formed of materials which are sufficiently durable as to safely and reliably facilitate a single use thereof, but which will not withstand the forces and pressures associated with repeated use thereof.

For example, the housing is preferably formed of an inexpensive and sufficiently durable (for a single use) polymer material, such as glass loaded acrylonitrile-butadiene-styrene (ABS) or such as polycarbonate. If the housing is formed of glass loaded acrylonitrile-butadiene-styrene (ABS), the acrylonitrile-butadiene-styrene (ABS) preferably comprises approximately 15% to approximately 20% glass. This particular formulation of acrylonitrile-butadiene-styrene (ABS) has been found to be sufficiently durable to reliably and safely facilitate a single use of the present invention, while being insufficiently durable as to facilitate indefinitely repeated use thereof. Further, both acrylonitrile-butadiene-styrene (ABS) and polycarbonate are sufficiently inexpensive as to facilitate the provision of a truly disposable device. The housing is preferably formed of two separate housing sections which are substantially mirror images of one another, so as to further mitigate cost. Preferably, multiple cavity injection molds are used to form the housing.

As discussed in detail below, the plunger and the two resilient cushions, all of which are preferably simultaneously co-molded to the shaft, are all formed of Santoprene. While Santoprene is sufficiently durable for a single use of the present invention, Santoprene is not sufficiently durable for indefinitely repeated use thereof. Repeated use of the present invention will result in degradation of the Santoprene components thereof and thus render the present invention unsuitable for further use. In particular, the cushions will tend to deform substantially with each use, such that they rapidly loose their ability to function as shock absorbers.

A trigger for the needleless injector of the present invention is preferably formed of stamped stainless steel sheet. Such a stamped stainless steel trigger is sufficiently durable as to facilitate single use thereof. The stamped stainless steel trigger is also sufficiently inexpensive as to facilitate the construction of a truly disposable device. The trigger may be polished, if desired, so as to enhance the appearance thereof, since the cost associated with such polishing is negligible.

The trigger is preferably formed in a stair-stepped configuration, so as to eliminate the need for a pivot pin therefor and thus further reduce costs, as discussed in detail below.

The spring injector mechanism preferably comprises a spring disposed within the housing, a piston configured to be moved by the spring and a shaft configured to be moved by the piston. The spring preferably comprises a closed, but not ground, music wire helical spring. Eliminating grinding of the spring further reduces cost without impairing the reliability or safety of the present invention.

The piston preferably comprises a die cast zinc, copper and aluminum alloy. The proportions of zinc, copper and aluminum are selected to provide the mass necessary to eject fluid from an ampule with the necessary force as to effect a subcutaneous injection. The use of such an alloy provides the necessary mass to drive the shaft in a manner that assures proper operation of the present invention, e.g., the development of pressure within the ampule of approximately 3,000–3,500 psi. The use of this alloy also reduces costs sufficiently to facilitate the construction of a disposable device.

The shaft preferably comprises polycarbonate having approximately 15% glass or a glass loaded polymer of equivalent performance such as Amodel (a federally registered trademark of Amoco Oil Company of Chicago, Ill.). The use of such a polycarbonate shaft provides sufficient durability to facilitate a single use of the present invention, while inhibiting indefinitely repeated use thereof. Further, this polycarbonate shaft reduces the cost of the needleless injector, so as to facilitate the construction of a truly disposable device.

According to the present invention, the shaft is a single piece or unitary construction member and extends completely through the housing and into the ampule. The shaft extends from the proximal end of the housing such that the spring injector mechanism may be cocked by pulling the shaft proximally. As mentioned above, the shaft is preferably configured so as to inhibit grasping thereof, in order to similarly inhibit cocking of the spring injector mechanism by a user. Rather, the spring injector mechanism is cocked at the factory by a machine which is specifically configured to grasp the proximal end of the shaft and pull the proximal end of the shaft proximally with respect to the housing.

Such single piece or integral construction of the shaft has a further advantage, in that it readily facilitates filling of the ampule with a desired quantity of medication in a simple and accurate manner. The ampule may be filled by manipulating the proximal end of the shaft. Manipulating the proximal end of the shaft similarly manipulates the distal end thereof, so as to draw fluid into the ampule or expel fluid from the ampule in a very precise manner.

The ampule is permanently attached to the housing, such that access to the distal end of the shaft is inhibited, thereby preventing the spring injector mechanism from being cocked by pushing the distal end of the shaft against a surface (as is done according to some contemporary needleless injectors) Permanently attaching the ampule to the housing further mitigates a danger associated with dry firing or actuating the needleless injector without medicine in the ampule. Although the shaft is driven forcible in the distal direction when the needleless injector is dry fired, the permanently attached ampule prevents the moving shaft from striking anything other than the ampule itself.

The ampule is preferably threadedly attached to the housing, and then either adhesively bonded or sonically welded thereto. Permanent attachment of the ampule to the housing not only enhances safety by mitigating the ability to fire the needleless injector with the ampule removed and facilitates single use of the needleless injector by inhibiting refilling of the ampule due to sterility concerns, but also reduces the cost of the present invention. The cost of the present invention is reduced by eliminating the need to form threads within the housing which are suitable for repeated attachment and removal of the ampule. That is, according to the present invention, the threads may merely be injected molded as a part of the two housing sections and need not be formed or touched up via machining or the use of a tap. Rather, the threads which are integrally injected molded with the two housing sections are sufficient for a single use of the present invention, particularly when the ampule is further attached to the housing via adhesive bonding and/or sonic welding. Indeed, the housing need not comprise any threads for attaching the ampule thereto, but rather may alternatively utilize any desired injection moldable structure for this purpose. For example, threads may be eliminated from both the housing and the ampule and the ampule may merely be inserted into the housing and permanently bonded thereto.

The needleless injector of the present invention is more particularly described below with reference to FIGS. 1–16 of the drawings, which depict a presently preferred embodiment thereof. FIGS. 17–21 depict a volume efficient package for the needleless injector of the present invention, so as to substantially reduce the transportation and storage cost associated therewith, and thereby further facilitate the provision of a truly disposable device. As shown in FIG. 1, the needleless injector of the present invention is provided to a user in a substantially ready-to-use condition, requiring only that the ampule be filled with a particular medicament prior to injection.

Referring now to FIGS. 1–13, the low cost disposable needleless injector 10 of the present invention generally comprises a housing 8 and a spring injector mechanism 9 disposed partially within the housing. The housing 8 is generally cylindrical, approximately four inches in length excluding the ampule, and approximately one-half inch in diameter. The ampule is approximately one and five-eighths inch in length and approximately three-eighths inch in diameter.

The housing 8 is shaped such that it is easily grasped in the hand of a user, and when appropriately oriented, presents a depressable trigger mechanism in the vicinity of the user's thumb or finger. Indeed, the housing and trigger are configured such that when the housing is grasped within a user's hand, the trigger may be depressed either by the thumb, a finger or by merely squeezing the device in the user's hand or fist. The trigger has sufficient surface area and leverage to make the present invention easily actuatable by the elderly, the very young and the infirm. Moreover, the configuration and positioning of the trigger readily facilitates actuation by persons in a debilitated or weakened state and is even suitable for use in emergencies since a user does not have to take time to carefully hold and/or position the device in a particular manner. The device may be held in any manner which is convenient for the person administering the injection. It is merely necessary that the device be held in close contact to the skin, preferably generally perpendicularly thereto, and that the trigger then be depressed. The trigger is positioned to facilitate use of the present invention for the self-administration of medicine, as well as to facilitate the administration of medicine to patients by healthcare workers in any desired manner, e.g., with a thumb, finger, or by squeezing the entire device in a person's hand or fist.

The housing 8 preferably comprises first and second housing sections which are preferably injection molded either from acrylonitrile-butadiene-styrene (ABS) loaded with approximately 15% to approximately 20% glass or is alternatively injection molded from polycarbonate. The housing 8 has a proximal end and a distal end as labeled in FIG. 1. All references to proximal and distal herein use these terms as defined in FIG. 1. It is the distal end of the device (more particularly, the distal end of the ampule 50) which is pressed against the skin of a person who is to receive an injection.

Forming the housing 8 as two separate housing sections reduces the complexity and cost associated with the molding process, since an unthreading mold would be required if a unitary construction housing were to be provided with female threads in order to receive the ampule. As those skilled in the art will appreciate, such unthreading molds are considerably more expensive than simple release molds, and would thus undesirably increase the cost of the needleless injector of the present invention.

An additional advantageous feature afforded by forming the housing as two separate housing sections is appreciated during the assembly process, wherein the device may be assembled by simply placing the components into one of the two housing sections and then positioning the other housing section thereover. The two housing sections are bonded to one another using adhesive, sonic welding, or any other desired method.

More particularly, the assembly process comprises inserting a shaft 25 through the piston 15. The resilient washers 31 and 32 and the plunger 26 have previously been co-molded or over-molded to the shaft of the shaft 25. The spring 13 is then slid over the sleeve 17 of the piston 15 so as to define the spring injector mechanism 9. The spring injector mechanism 9 is then placed into one of the two housing sections. The safety slide 42 and the trigger 40 are similarly placed in the same housing section. The other housing section is then mated thereto and bonding is effected. The ampule may then be screwed into the housing and bonded thereto. Alternatively, both the ampule and the housing may lack threads, such that the ampule may simply be slid into the housing and bonded thereto. Those skilled in the art will appreciate that various different mechanical locking means for permanently attaching the ampule to the housing are likewise suitable. Thus, the ampule may be mechanically locked to the housing and/or bonded thereto. Then the needleless injector of the present invention may be cocked utilizing a machine which holds the housing in place, while pulling the shaft 25 proximally, by grasping the ball 27 thereof. With the shaft 25 held in the cocked position, the trigger 40 is moved to a position wherein the sear 37 thereof inhibits distal movement of the piston 15 and the safety slide 42 is moved distally, so as to prevent undesirable movement of the trigger 40.

Figure 14:
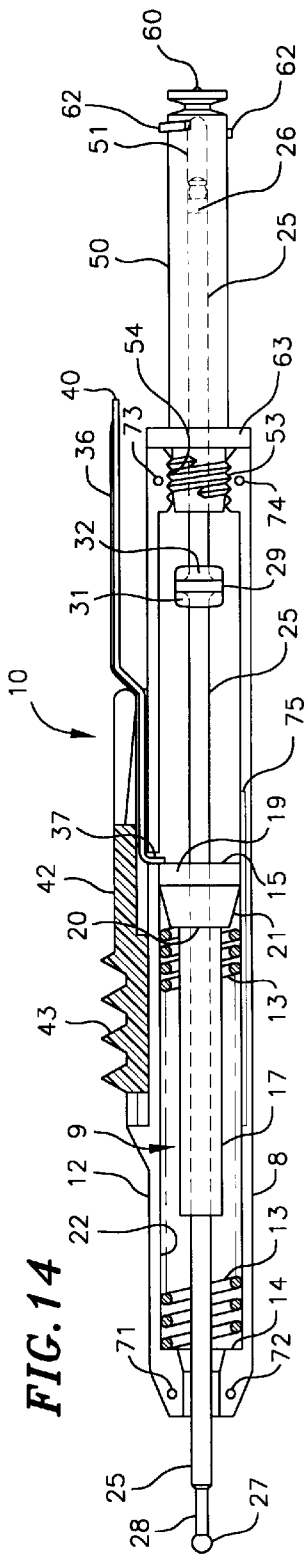
FIG. 14 is a semi-schematic cross-sectional side view of the needleless injector of FIG. 1, wherein the shaft is positioned within the ampule at a location corresponding to approximately 0.05 ml of medication being present in the ampule.
Figure 15:
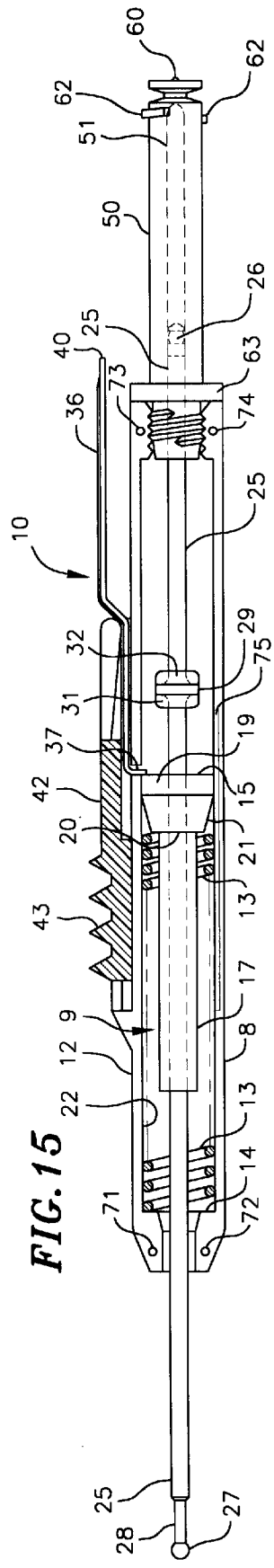
FIG. 15 is a semi-schematic cross-sectional side view of the needleless injector of FIG. 1, wherein the shaft is positioned within the ampule at a location corresponding to approximately 0.30 ml of medication being present in the ampule.
Figure 16:
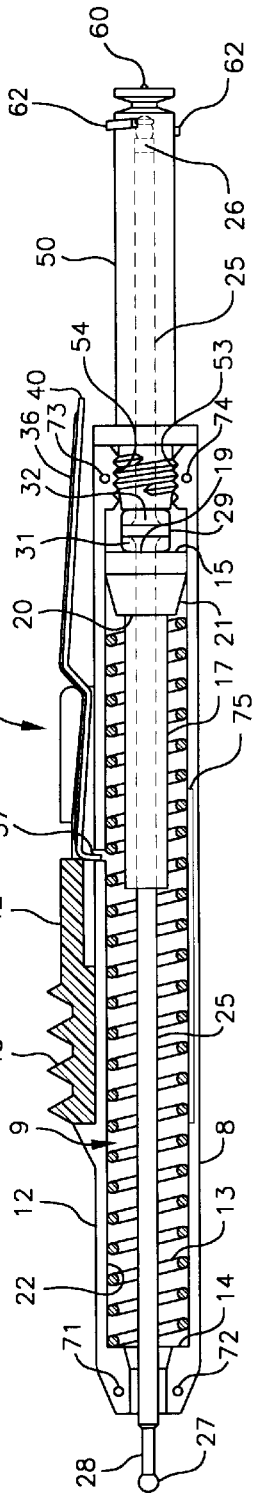
FIG. 16 is a semi-schematic cross-sectional side view of the needleless injector of FIG. 1, showing the configuration of the trigger, spring, piston, and shaft after the trigger has been depressed so as to actuate the spring injector mechanism.

The spring is preferably a closed, but not ground, music wire helical spring 13 (best shown in FIGS. 5 and 14–16) which is disposed within the housing such that the spring 13 has a cocked or compressed configuration, as shown in FIGS. 5, 14 and 15 and also has a fired or uncompressed configuration as shown in FIG. 16. The spring 13 preferably has a spring constant of approximately 24 lbs./in. The spring is preferably approximately 3 inches long and develops approximately 28 lbs. of force when compressed so as to cock the spring injection mechanism. The spring 13 is sized to slide freely within a bore 22 of the housing. The proximal end of the spring 13 bears upon shoulder 14 formed within the housing and the distal end of the spring 13 bears upon a piston 15 (best shown in FIG. 9).

The piston 15 comprises a sleeve 17 which is sized to be received within the spring 13. The sleeve 17 preferably has an outside diameter which is substantially less than the inside diameter of the coil formed by the spring 13, such that the sleeve 17 moves freely along the inside of the spring without substantially frictionally engaging the spring 13.

The piston further comprises a head 19 which defines a shoulder 20 against which the distal end of the spring 13 abuts. The head 19 of the piston 15 is sized to slide freely within the bore 22. The piston optionally further comprises a conically tapered portion 21 of the head 19. However, those skilled in the art will appreciate that the exact configuration, size and dimensions of the piston 15 will be determined, as least in part, by the mass thereof which is required to eject fluid from an ampule 50 with the necessary force to reliably perform an injection. Thus, the mass of the piston 15 is determined by both its dimensions and the materials from which it is formed, as discussed above.

The ampule 50 is preferably substantially transparent, so as to facilitate viewing of the quantity of liquid contained therein. A scale is typically provided upon the ampule so as to provide a numerical indication of the quantity (typically in milliliters) of fluid contained therein.

The spring injector mechanism 9 further comprises an elongated shaft 25 (best shown in FIG. 7) having a plunger 26 (best shown in FIG. 8) formed upon the distal end thereof and having a cocking knob 27 formed upon the proximal end thereof. The plunger 26 is preferably formed of an elastomer or thermosetting rubber such as Santoprene manufactured by Sonoco or the equivalent.

The plunger 26 is secured firmly to the shaft 25 via a shaft retaining heads 90a and 90b formed at the distal end of a portion 91 of the shaft 25 having a reduced diameter, as discussed in detail below.

The gripping ball 27 is preferably formed upon the proximal end of the shaft 25 by forming a reduced diameter neck 28 formed in the shaft 25 near the proximal end thereof. The shaft 25 further comprises a portion of increased diameter or shoulder 29 formed thereon and disposed within the housing. The shoulder 29 is preferably formed integrally with the shaft 25. Alternatively, the shoulder 29 may be formed separately from the shaft 25 and be attached thereto. Resilient cushions 31 and 32 are preferably disposed upon either side of the shoulder 29. Resilient cushion 31 cushions the impact of the piston 15 when the piston moves forward and strikes the shoulder 29 of the shaft 25 so as to cause the shaft 25 to eject fluid, as described in detail below. Similarly, resilient cushion 32 cushions the impact of the shoulder 29 of the shaft 25, when the shoulder 29 strikes a proximal portion of the ampule 50 during the fluid injection process, as also discussed in detail below. Both resilient cushions, 31 and 32, thus cooperate to mitigate noise and recoil when the device is operated. The mitigation of noise and recoil is important, so that the device is perceived as user friendly. Those skilled in the art will appreciate that excessive noise and recoil may be associated with pain or discomfort, and are thus undesirable.

As shown in FIG. 1, the needleless injector 10 of the present invention is configured as it is typically packaged and received by a user. The ampule 50 is empty, i.e., contains no medication when configured for variable dose applications, and the shaft 25 is disposed partially within the ampule 50 so as to reduce the overall length of the device to facilitate volume efficient packaging thereof.

The first and second resilient cushions, 31 and 32, as well as the plunger 26, are all preferably injection molded to the shaft 25 during a single injection co-molding process, and thus all preferably comprise the same resilient thermosetting rubber material, e.g., Santoprene (a federally registered trademark of Monsanto Company of St. Louis, Mo.). The plunger 26 and the first and second cushions, 31 and 32, may alternatively be formed of polyvinyl chloride (PVC) or silicone. With particular reference to FIG. 8, the plunger 26 preferably comprises a central bore 24 ending in distally located hemispherical chambers 34a and 34b. The bore 24 is configured to receive the reduced diameter portion 91 of the shaft 25 and the chambers 34a and 34b are configured to receive the heads 90a and 90b of the shaft 25, in a manner which facilitates secure attachment of the plunger 26 to the shaft of the shaft 25. The heads 90a and 90b of the plunger 25 preferably define a Christmas tree or conically barbed protrusion, such as those commonly used to facilitate the attachment of an elastomeric component to a more rigid member.

The piston 15 is held in the cocked position thereof, against the force of spring 13 by the trigger 40, which is preferably formed of stamped stainless steel. Preferably a rib 36 is formed longitudinally along a substantial portion of the length of the trigger 40, so as to enhance the structural strength thereof. As those skilled in the art will appreciate, the use of such a rib 36 allows the trigger 40 to be formed of substantially thinner sheet stainless steel, thereby further reducing the cost thereof.

As best shown in FIG. 11, the trigger is formed in a stair-step like fashion, so as to define a sear 37, a lower portion 38, a middle portion 39 and an upper portion 40. This stair-step configuration of the trigger 35 facilitates reliable use thereof without the need for a pivot pin, so as to further mitigate costs.

Safety slide 42 (best shown in FIG. 10) is slideably attached to the housing such that the safety slide has a distal position wherein movement of the trigger 40 is inhibited so as to likewise inhibit actuation of the spring injection mechanism, and also has a proximal position, wherein the trigger is free to move, as discussed in detail below. The distal position at the safety slide 42 thus mitigates the likelihood of inadvertent actuation of the spring injector mechanism. The safety slide 42 preferably has ridges 43 formed thereon, so as to facilitate easy operation thereof.

A flange 48 extends distally from the safety slide 42. When the safety slide 42 is in its safe or distalmost position, the flange 48 covers a portion of the trigger 40, so as to inhibit actuation of the injector spring mechanism, as discussed in detail below.

Female detents 47 (there is preferably one female detent on each side of the safety slide, cooperate with corresponding male detents formed upon the first and second housing sections to releasably lock the safety slide in the safe position (the distal most position) thereof, so as to inhibit inadvertent movement of the safety slide away from the safe position thereof.

The ampule 50 (best shown in FIGS. 13 and 14–16) has a chamber 51 formed longitudinally therein for containing medication. The ampule 50 is preferably permanently attached to the housing via threads 53 formed upon the proximal end thereof and complementary threads 54 (best shown in FIG. 6) formed at the distal end of the housing. In addition to threadedly attaching the ampule 50 to the housing, the ampule is preferably adhesively bonded and/or sonically welded to the housing, so as to assure permanent attachment thereof.

As used herein, permanent attachment of the ampule to the housing is defined as attachment of the ampule to the housing via bonding, such as adhesive bonding or sonic welding, and/or via mechanical fastening, in a manner which substantially inhibits removal of the ampule from the housing by a user.

Indeed, according to the present invention the ampule is preferably attached to the housing in such a manner that the ampule is not likely to be removed from the housing by a user without damaging the device and rendering it unuseable.

The ampule 50 further comprises a tip 60 formed at the distal most end thereof. The tip 60 has a bore formed therein so as to facilitate fluid communication of the medicine from the chamber 51 and therethrough during the injection process.

A Luer like threaded fitting or lug 62 is preferably formed proximate the distal end of the ampule, so as to facilitate filling thereof. The ampule is preferably formed of polycarbonate and optionally comprises a contemporary ampule such as those commonly used in needleless injection devices.

Generally, the ampule is filled by affixing a transfer coupler to the front end of the ampule and using the transfer coupler to access the contents of either a standard drug vial, standard syringe cartridge, or the like. Once the contents of the medication container are accessed, the injection device is filled by manipulating the shaft 25. The shaft 25 is withdrawn or moved proximally so as to create a suction in the chamber 51 of the ampule 50, so as to effect extraction of medication from the medication container.

For example, a user may move the shaft 25 to its distal most position, thereby forcing substantially all of the air from the ampule. The user may then move the shaft 25 proximally, so as to produce suction within the chamber 51 of the ampule 50 and thus effect withdrawal of medication from a vial into the chamber 51. Typically, the ampule will be filled within slightly more medication then is necessary for the desired injection, so that any air in the ampule can be ejected by simply holding the needleless injector vertical, with the ampule uppermost, and then pushing the shaft back into the ampule chamber slightly, so as to effect ejection of any air within the ampule, as well as a small quantity of medicine, as those skilled in the art will appreciate. The user may then verify that the correct dosage has been withdrawn into the ampule by viewing the position of the plunger 26 within the ampule, relative to the graduations that are preferably provided upon the transparent ampule. Since the ampule is generally overfilled slightly, the user may reduce the quantity of medicine contained within the ampule by simply pushing the shaft 25 distally.

Figure 6:
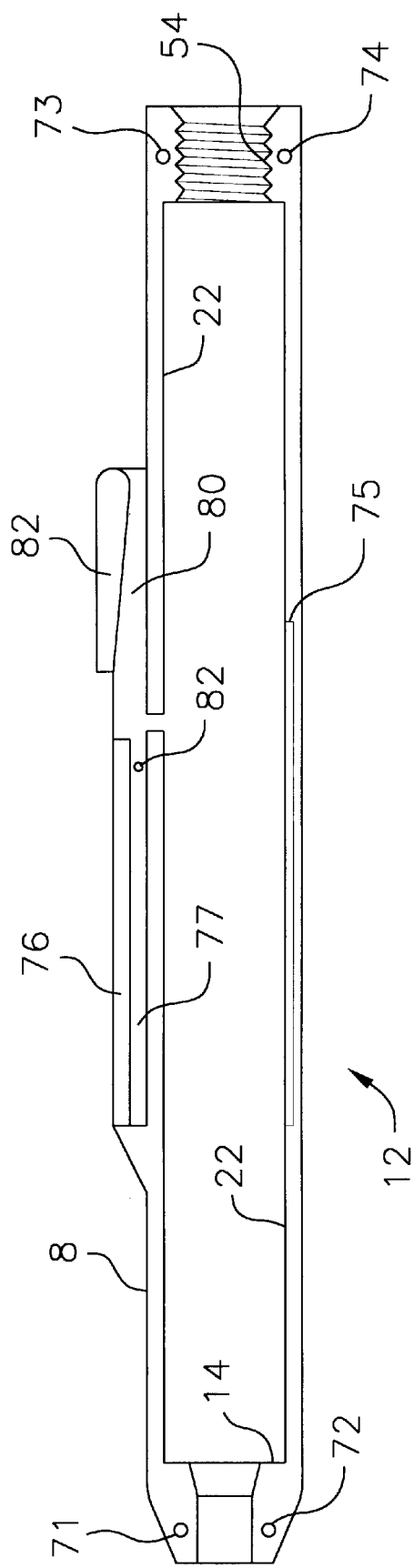
FIG. 6 is a semi-schematic side view of one housing section; i.e., the housing section opposite that which is shown in FIG. 1.

With particular reference to FIG. 6, the housing preferably comprises a second housing section 12, which is substantially a mirror image of the first housing section 11. One distinction between the first and second, 11 and 12, housing sections is that one of the two housing sections has first, second, third and fourth guide pins, 71, 72, 73 and 74, as well as guide slat 75 formed thereon. These guide members comprise male guide members, while on the other one the two housing sections, 12 and 11, complimentary female guide members are formed. The male and female guide members engage one another, so as to facilitate proper alignment of the two housing sections and so as to maintain the two housing sections in such proper alignment during sonic welding of the first and second, 11 and 12, housing sections to one another.

Each housing section, 11 and 12, comprises a groove 77 within which the safety slide 42 is slideably disposed. A male detent 82 is preferably formed within the groove 77 of each housing section so as to engage a corresponding female detent 47 of the safety slide 42 in a manner which releasably locks the safety slide 42 in the safe position, as discussed above. Safety slide 42 comprises first 78 and second 79 flanges which are received within the slots 77 of the first and second housing sections to facilitate slidable movement of the safety slide 42.

Both the first and second housing sections further comprise a tapered slot 80 within which the trigger 35 is pivotally disposed, as shown in FIGS. 5 and 14–16. The tapered slot 80 facilitates pivoting of the trigger 35, in a see-saw like fashion, about angled edge 81 (FIG. 11) of the trigger such that when the distal end of the trigger 35 is depressed or pushed toward the housing, then the proximal end of the trigger 35, including the sear 37 thereof, moves upwardly, so as to effect disengagement of the sear 37 from the piston and thereby actuate or fire the spring injection mechanism to effect an injection.

The needleless injector cannot easily be used more than one time due to the difficulty associated with re-cocking thereof and/or due to the unsuitability of the materials and/or design for repeated reuse.

The needleless injector of the present invention is formed utilizing a minimum number of components, such that it may be manufactured in a simple fashion by unskilled workers.

Having described the structure of the low cost, disposable needleless injector in detail above, it may be beneficial to likewise describe the operation thereof. Operation of the needleless injector is described below with reference to FIGS. 14–16.

With particular reference to FIG. 14, the needleless injector 10 is shown with the shaft 25 positioned within the ampule 50 in a manner which facilitates the injection of a comparatively small amount, e.g., 0.05 ml, of medicine. Similarly, FIG. 15 shows the shaft 25 positioned within the ampule 50 in a manner which facilitates the injection of a comparatively larger amount of medicine, e.g., approximately 0.30 ml. Thus, the shaft 25 can be moved to various positions within the ampule 50, so as to facilitate the injection of various different quantities of medication, as is necessary for variable dose usage.

In both FIGS. 14 and 15, the spring 13 is compressed intermediate the shoulder 14 of the housing and the shoulder 20 of the piston 15. The piston 15 is maintained in this cocked position by the sear 37 of the trigger 40. The safety slide 42 prevents actuation of the spring injector mechanism by preventing the trigger 40 from being depressed toward the housing and thereby preventing the sear 37 from disengaging the piston 15. Thus, the safety slide 42 tends to prevent accidental actuation of the spring injector mechanism, which might result in accidental injection of the medicine. In any event, accidental actuation of the spring injector mechanism of the present invention will render the device unusable, since the low cost disposable needleless injector of the present invention is specifically configured for only a single use thereof.

The ampule 50 of the needleless injector of the present invention is loaded with medicine by attaching a vial or the like to the distal end of the ampule 50 and moving the shaft 25 proximally, so as to draw medicine from the vial into the ampule 50, according to well known principles.

Since the ampule is permanently affixed to the needleless injector of the present invention, there is no need for a user to have to insert, attach, or otherwise adapt the ampule to an injector, in order to perform an injection.

Preferably, the shaft 25 is placed in its distal most position prior to attaching the ampule 50 to the vial, such that there is very little or no air within the chamber 51 of the ampule 50. The quantity of medicine with which the ampule 50 is filled can be read accurately from a scale (FIG. 13) formed upon the ampule 50. The ampule 50 may be slightly over filled, if desired.

After filling the ampule, the injection site upon the person receiving the injection and/or the distal end of the ampule 50 are sterilized, such as with alcohol, and the injection is then administered.

The injection is administered by holding the needleless injector 10 generally perpendicular to the skin at the injection site and then depressing the trigger 40, such as with the thumb of the hand holding the device. Prior to depressing the trigger, the safety slide 42 must be moved proximally, so as to allow the sear 37 to disengage the piston 15.

After the trigger 40 has been depressed, and the sear 37 disengages the piston 15, the spring 13 moves from its compressed position (as shown in FIGS. 14 and 15) to its uncompressed or extended position as shown in FIG. 16. As the spring 13 moves toward its uncompressed position, the spring 13 urges the piston 15 distally. As the piston 15 moves distally, the piston 15 strikes the first resilient washer 31 and causes the shaft 25 to move distally along with the piston 15. The first resilient washer 31 cushions the impact of the piston 19 with respect to the shoulder 29 of the shaft 25.

It will be noted that there is a gap between the piston 15 and the shoulder 29, as shown in both FIGS. 14 and 15. This gap is the distance that the piston 15 must travel before it strikes the cushion 31, which is located just proximal of the shoulder 29. The length of the gap is within a range of gap lengths which are defined by the position of the plunger 26 within the ampule, as determined by the quantity of medication to be injected. Each gap length within this range of gap lengths is suitable for allowing the piston 15 to accelerate sufficiently before striking the cushion 31, so as to generate the desired pressure (typically approximately 3,000 psi–5,000 psi) within the chamber 51 of the ampule 50.

As the spring 13 continues to move toward its extended position, the plunger 26 expels the medicine from the chamber 51 of the ampule 50, thereby effecting the injection.

According to the preferred embodiment of the present invention, the spring 13 remains partially compressed in its fully extended position (as shown in FIG. 16) and therefore has a preload.

It is important to appreciate that after the injection has been effected, it would be extremely difficult for a user to re-cock the spring injector mechanism so as to effect the performance of another injection with the needleless injector of the present invention. The proximal end of the shaft 25 is specifically configured to inhibit grasping thereof, as is necessary to effect re-cocking of the device.

Further, permanent attachment of the ampule 50 to the housing prevents the attachment of a new, sterile ampule to the housing, as would be desirable in the performance of another injection.

Figure 17:
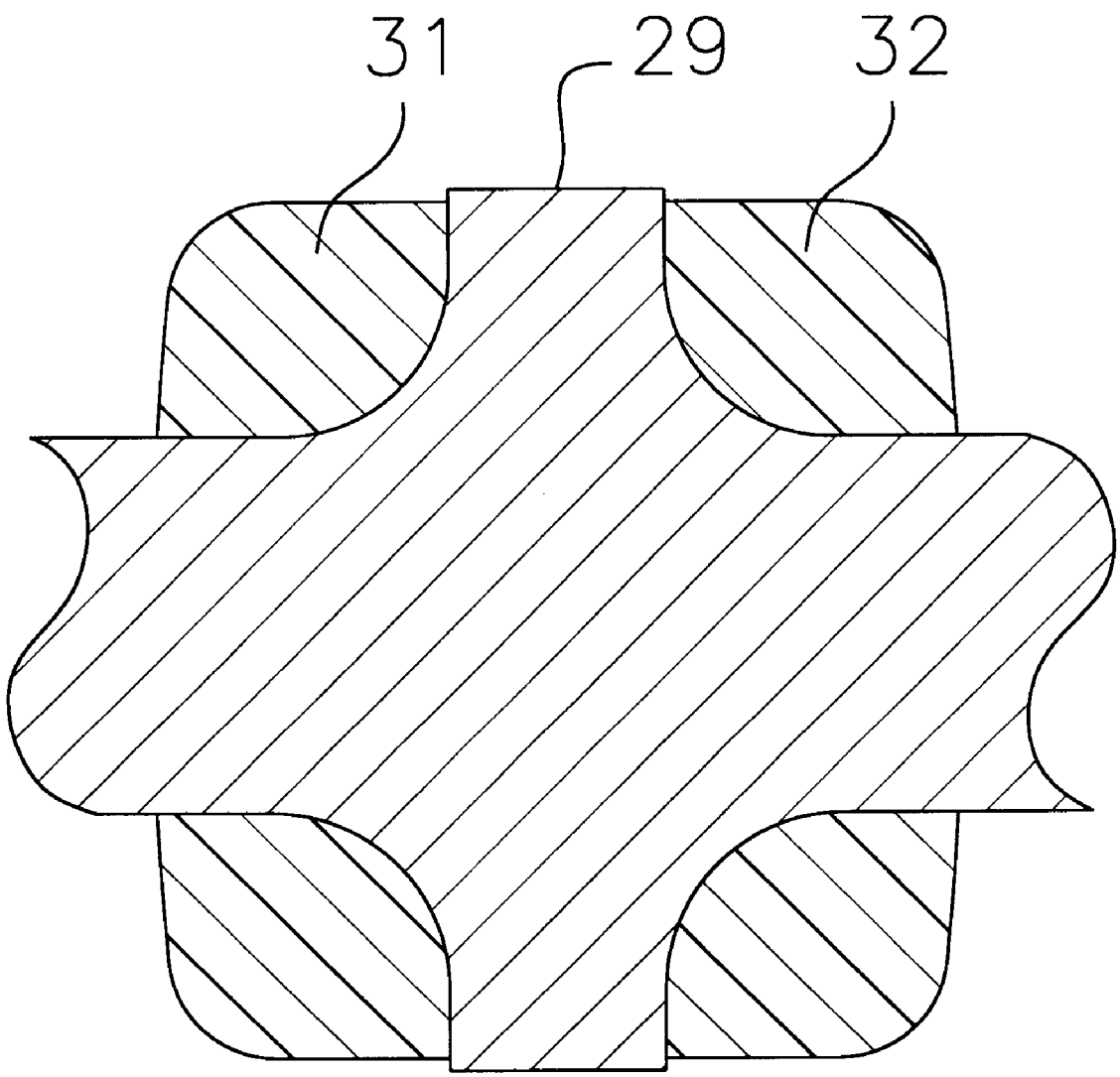
FIG. 17 is a semi-schematic cross-sectional view showing the shoulder 29 and the cushions, 31 and 32.
Figure 20:
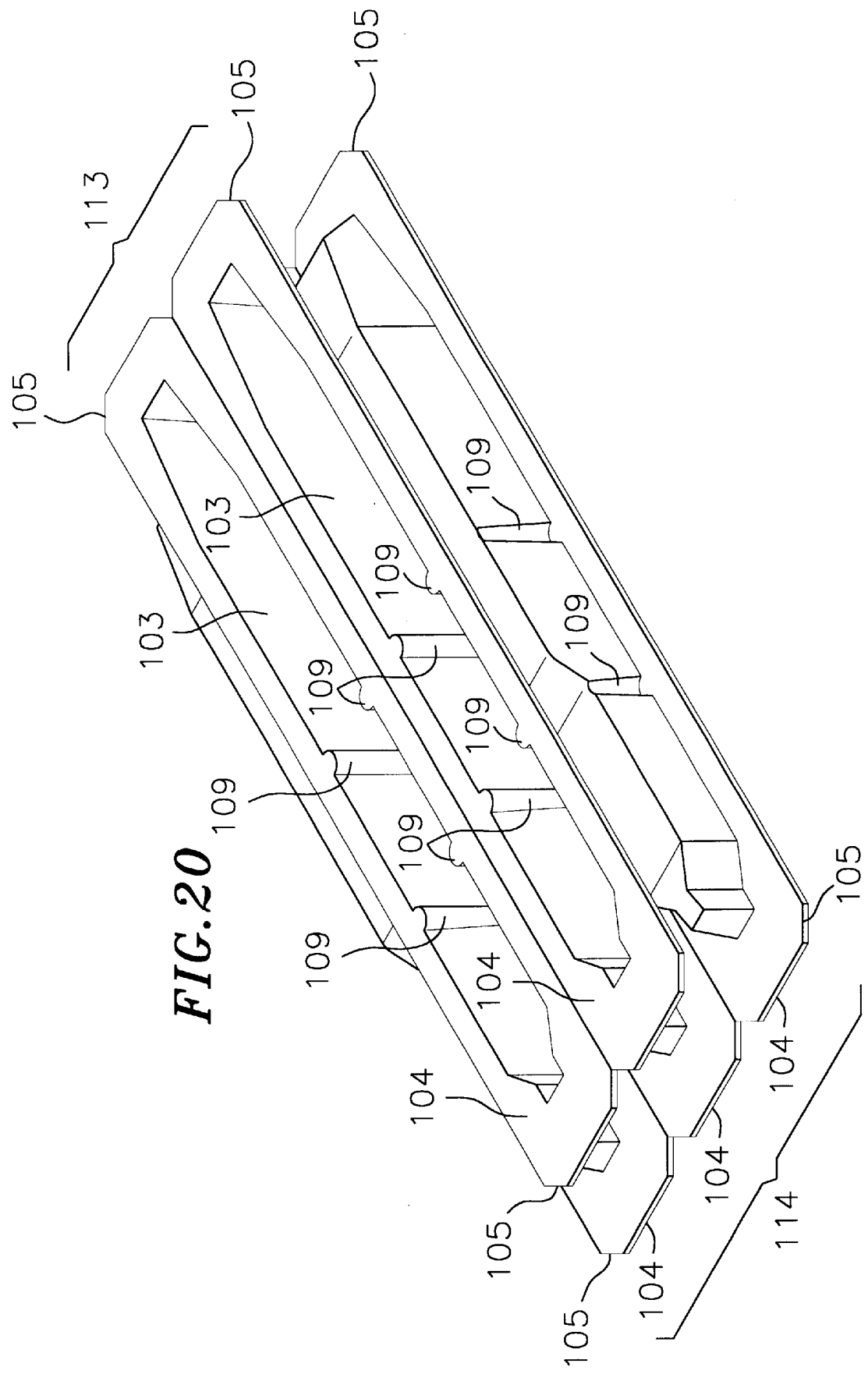
FIG. 20 is a semi-schematic perspective view of the cluster of packages of FIG. 19, which has been rotated 180° about the longitudinal axis thereof.

Referring now to FIG. 17, the shoulder 29 is shown to be integrally formed with the shaft 25. Those skilled in the art will appreciate that various other means of forming such a shoulder upon a shaft are likewise suitable. For example, the should may alternatively be formed by adding a separately formed structural member to the shaft 25. The cushions 31 and 32 are molded directly to the shaft 25 and the shoulder 29, as discussed in detail above.

Referring now to FIGS. 18–22, volume efficient packaging for the needleless injector of the present invention is shown. As those skilled in the art will appreciate, it is important to reduce the various costs associated with use of the needleless injector of the present invention, so as to make disposability thereof economically feasible. One important aspect of such cost reduction involves the use of volume efficient packaging, so as to mitigate transportation and storage costs associated with the present invention.

The packaging system of the present invention has been specifically designed so as to minimize the cost and the volume associated with the packaging. Thus, according to the present invention, each package, as shown in FIG. 18 requires only slightly more volume than the needleless injector itself. Further, a cluster of packages as shown in FIGS. 19 and 22 comprises interleaved individual packages which further minimize wasted space.

Wasted space is minimized in the cluster of packages by inserting or interleaving one row of packages along with another row thereof. Thus, space between adjacent packages within a row, which is normally wasted, is efficiently utilized according to the present invention. That is, a needleless injector in one row of packaging according to the present invention is disposed efficiently intermediate two adjacent needleless injectors of the other row thereof.

With particular reference to FIG. 18, each individual package 100 for a needleless injector 10 according to the present invention, comprises a cradle 101 and a cover 102. The cover 102 is preferably bonded, such as via adhesive bonding to a planar surface 104 of the cradle 101. The cradle 101 defines a cavity 103. The cover 102 completely covers and hermetically seals the cavity 103, so as to facilitate the provision of a sterile environment for the needleless injector contained therein. Both the cradle 101 and the cover 102 are preferably transparent, so that the presence of a needleless injector within the package 100 is easily detected.

Each cradle 101 is preferably formed by vacuum forming sheet polymer material. Each cover 102 is preferably formed by cutting, die stamping or otherwise forming individual covers from roll or sheet polymer.

According to the preferred embodiment of the present invention, each corner of the cradle 101 comprises a bevel 105 which exposes a corresponding corner 107 of the cover 102, so that the cover 102 may be easily grasped and peeled away from the cradle 101, as shown in FIG. 18.

The cradle preferably further comprises a plurality of ribs 109, which enhance the structural strength thereof, and thus facilitate the use of thinner material in the construction of the cradle, so as to further reduce the cost thereof.

The cavity 103 of the cradle 101 generally conforms in shape to the shape of the needleless injector, so as to minimize the cost of the packaging, as well as the volume thereof.

When a plurality of such packages are placed in a row, i.e., side by side, then a gap is formed between adjacent packages. As discussed below, the present invention takes advantage of this gap between adjacent packages so as to further enhance the volumetric efficiency associated with the packaging of a plurality of needleless injectors.

With particular reference to FIGS. 19–22, a plurality of packages, such as those of FIG. 18, are formed together in a cluster 110. The cluster may comprise either a plurality of individual packages, which have been attached to one another, or may alternatively comprise one or more pluralities of individual packages which are formed together, integrally with one another. For example, the cluster 110 may comprise two pluralities of packages or rows, 113 and 114, wherein each row, 113 and 114, is formed integrally and separately from each other row, 114 and 113, and then the two rows are attached to one another or interleaved. Thus, each row, 113 and 114, of the cluster 110, may be formed separately by vacuum forming or the like, and then the rows may be interleaved. This interleaving of the two rows enhances the volume efficiency of the completed multiple needleless injector package is thus more volume efficient and less costly.

The covers for each cradle in a row are either separately formed or are formed of one piece of material which is perforated or scored, such that the individual cover associated with a particular needleless injector may be peeled away from the cradle so as to facilitate the removal of a desired particular needleless injector. The use of such separate covers for each needleless injector facilitates the storage of the remaining needleless injectors in a sterile environment after one or more of the needleless injectors has been removed from such a cluster package.

The clusters may be formed such that they are easily broken apart, so as to form individual packages or so as to form smaller clusters. Scores or perforations may be utilized so as to facilitate such breaking apart of a cluster. A cluster so scored or perforated may be formed so as to break apart into smaller clusters having any desired number of individual packages.

The cradles are preferably formed from a transparent polymer material such as polyethylene terephalate glycol (PETG). The covers are preferably comprised of a material such as Tyvek (a federally registered trademark of Dupont de Nemurs and Company of Wilmington, Del.).

According to the present invention, all of the components of the present invention, including the components of the packaging, are suitable for gamma sterilization. The needleless injector of the present invention is packaged, either automatically or manually, by placing one needleless injector in the cavity of each cradle and then sealing the cover to the upper flat surface 104 of each cradle, so as to provide a hermetic seal. After hermetically sealing a needleless injector in each package of a cluster (or in a non-cluster, single product package), then the needleless injector(s) and associated package(s) are gamma sterilized. Gamma sterilization is performed after sealing of the needleless injectors within their packages so as to assure maintenance of proper sterilization thereof, until the packages are opened by the user.

According to an alternative configuration of the present invention, the needleless injector may be provided to the user with the ampule aneseptically filled with a desired medicament. When the needleless injector is provided with the ampule prefilled, then the proximal most portion of the shaft 25 is preferably cut off or otherwise removed, so as to inhibit movement thereof, which might tend to undesirably force fluid from the ampule. That is, that portion of the shaft 25 which would otherwise extend from the proximal end of the housing is removed, so as to prevent the shaft 25 from being undesirably manipulated during handling. In this manner, fixed dose applications of the present invention are facilitated.

It is understood that the exemplary low cost, disposable needleless injector described herein and shown in the drawings represents only a presently preferred embodiment of the invention. Indeed, various modifications and additions may be made to such embodiment without departing from the spirit and scope of the invention. For example, various different configurations of the spring, piston and shaft are contemplated. For example, those skilled in the art will appreciate that the piston may have various different configurations, shapes and/or dimensions which facilitate compression of the spring, locking of the spring in the compressed configuration thereof by the trigger, and which have the necessary mass so as to assure proper ejection of a fluid from the ampule when the shaft is struck thereby.

Thus, these and other modifications and additions may be obvious to those skilled in the art and may be implemented to adapt the present invention for use in a variety of different applications.

What is claimed:

1. A needleless injector comprising:
   a housing;
   a spring injector mechanism including a shaft disposed at least partially within the housing and at least partially externally of the housing, the spring injector mechanism being configured to be used only one time; and
   wherein said shaft is configured to move in any axial direction even when said spring injector mechanism is in a cocked position by grasping and moving the partially externally portion of the shaft.

2. The needleless injector as recited in claim 1, wherein the spring injector mechanism is configured to inhibit cocking by a user.

3. The needleless injector as recited in claim 1, wherein the spring injector mechanism is configured to require a tool to facilitate cocking thereof.

4. The needleless injector as recited in claim 1, wherein at least one of the housing and the spring injector mechanism is configured to be unsuitable for repeated use thereof.

5. The needleless injector as recited in claim 1, wherein at least one of the housing and the spring injector mechanism is configured to be unsuitable for indefinitely repeated use thereof.

6. The needleless injector as recited in claim 1, wherein at least one of the housing and the spring injector mechanism is formed of material which inhibits repeated use thereof.

7. The needleless injector as recited in claim 1, wherein at least one of the housing and the spring injector mechanism is formed so as to be insufficiently durable as to facilitate repeated use thereof.

8. The needleless injector as recited in claim 1, wherein the housing is formed of a polymer material.

9. The needleless injector as recited in claim 1, wherein the housing comprises two injection molded polymer housing sections which are sonically welded to one another.

10. The needleless injector as recited in claim 1, wherein the housing is formed of glass loaded acrylonitrile-butadiene-styrene (ABS).

11. The needleless injector as recited in claim 1, wherein a trigger is formed of stamped sheet metal.

12. The needleless injector as recited in claim 1, wherein a trigger is formed of stamped sheet stainless steel.

13. The needleless injector as recited in claim 1, wherein a trigger is formed in a stair-stepped configuration to eliminate a need for a pivot pin therefor.

14. The needleless injector as recited in claim 1, wherein the spring injector mechanism comprises:
   a spring disposed within the housing;
   a piston configured to be moved by the spring; and
   a shaft configured to be moved by the piston.

15. The needleless injector as recited in claim 1, wherein the spring injector mechanism comprises:
   a spring disposed within the housing;
   a piston configured to be moved by the spring; and
   a glass reinforced polymer shaft configured to be moved by the piston.

16. The needleless injector as recited in claim 1, wherein the spring injector mechanism comprises:
   a spring disposed within the housing;
   a piston configured to be moved by the spring; and
   a shaft configured to be moved by the piston;
   wherein the shaft is configured to inhibit grasping thereof so as to inhibit cocking of the spring injector mechanism.

17. The needleless injector as recited in claim 1, further comprising an ampule from which the shaft forces fluid when the shaft is moved.

18. The needleless injector as recited in claim 1, further comprising an ampule permanently attached to the housing.

19. The needleless injector as recited in claim 1, further comprising an ampule threadedly attached and adhesively bonded to the housing.

20. The needleless injector as recited in claim 1, further comprising an ampule threadedly attached and sonically welded to the housing.

21. The needleless injector as recited in claim 1, wherein the spring injector mechanism comprises a closed, but not ground, music wire helical spring.

22. The needleless injector as recited in claim 1, wherein:
   the housing comprises:
      two housing sections formed of injection molded plastic and configured to be substantially mirror images of one another;
   the spring injector mechanism comprises:
      a spring disposed within the housing;
      a piston configured to be moved by the spring; and
      a shaft configured to be moved by the piston.

23. A needleless injector comprising:
   a housing;
   a spring injector mechanism comprising a shaft, a piston, and a spring disposed at least partially within the housing and at least partially outside of the housing, the spring injector mechanism being configured to cause fluid to be injected; and
   wherein the spring injector mechanism is cocked by grasping at least a portion of the shaft that is outside of the housing, and the shaft, subsequent to the cocking, remains moveable relative to the piston.

24. A needleless injector comprising:
a polymer housing having proximal and distal ends;
an aluminum piston slidably disposed within the housing;
a music wire helical spring disposed within the housing and configured to urge the piston toward the distal end of the housing when the spring is released;
a glass reinforced polymer shaft disposed at least partially within the housing and partially outside of the housing and configured to be moved distally by the piston;
a stamped sheet steel trigger attached to the housing and configured to release the spring; and
wherein the injector is cocked by pulling on the shaft section that is partially outside of the housing which pulls the piston until the piston is engaged by the trigger; and
wherein the shaft remains movable in any axial direction even after the injector is cocked.

25. A low cost, disposable needleless injector system comprising:
a needleless spring injector mechanism;
an ampule permanently attached to the needleless spring injector mechanism from which fluid is forced by the needleless spring injector mechanism, and
wherein said spring injector mechanism includes a shaft and wherein said shaft is configured to be pulled to cock the spring injector mechanism and wherein the shaft remains moveable subsequent to the cocking of the spring injector mechanism.

26. The low cost, disposable needleless injector system as recited in claim 25, wherein the ampule is adhesively bonded to the needleless spring injector.

27. The low cost, disposable needleless injector system as recited in claim 25, wherein the ampule is sonically welded to the needleless spring injector.

28. The low cost, disposable needleless injector system as recited in claim 25, wherein the ampule is integrally formed with respect to the needleless spring injector.

29. A needleless injector system comprising:
a housing having proximal and distal ends;
a piston slidably disposed within the housing;
a spring disposed within the housing and configured to urge the piston toward the distal end of the housing when the spring is released;
a shaft configured to cock the needleless injector system disposed at least partially within the housing and partially outside of the housing and configured to be moved distally by the piston;
a trigger attached to the housing and configured to release the spring;
an ampule disposed proximate the distal end of the housing and configured to receive at least a portion of the shaft;
wherein when the shaft moves toward an aperture of the ampule, fluid disposed within the ampule is forced therefrom through the aperture; and
wherein the housing, piston, spring, shaft and trigger are configured to generally provide only one injection by configuring a proximal end of the shaft with a surface that is sufficiently small to limit a user's ability to generate sufficient cocking force with the user's bare hand.

30. A method for performing an injection, the method comprising:

releasing a spring force to thereby move a shaft that is partially coaxially disposed within a piston and adapted to move relative to the piston;
injecting fluid with a needleless spring injector; and
disposing of essentially all of the needleless injector after injecting the fluid only one time.

31. The method as recited in claim 30, wherein the needleless spring injector is configured to be disposable.

32. The method as recited in claim 30, wherein the step of injecting fluid with a needleless spring injector comprises moving a trigger so as to release a compressed spring, the spring moving a piston toward a distal end of the needleless spring injector, the piston moving a shaft to toward the distal end of the needleless spring injector and the shaft forcing fluid from an ampule.

33. The method as recited in claim 30, wherein the needleless spring injector comprises:
a housing; and
a spring injector mechanism disposed at least partially within the housing, the spring injector mechanism being configured to be used only one time.

34. The method as recited in claim 33, wherein the spring injector mechanism is configured to inhibit cocking by a user.

35. The method as recited in claim 33, wherein the spring injector mechanism is configured to require a tool to facilitate cocking thereof.

36. The method as recited in claim 33, wherein at least one of the housing and the spring injector mechanism is configured to be unsuitable for repeated use thereof.

37. The method as recited in claim 33, wherein at least one of the housing and the spring injector mechanism is configured to be unsuitable for indefinitely repeated use thereof.

38. The method as recited in claim 33, wherein at least one of the housing and the spring injector mechanism is formed of material which inhibits repeated use thereof.

39. The method as recited in claim 33, wherein at least one of the housing and the spring injector mechanism is formed so as to be insufficiently durable as to facilitate repeated use thereof.

40. The method as recited in claim 33, wherein the housing is formed of a polymer material.

41. The method as recited in claim 33, wherein the housing comprises two injection molded polymer housing sections which are sonically welded to one another.

42. The method as recited in claim 33, wherein the housing is formed of glass loaded acrylonitrile-butadiene-styrene (ABS).

43. The method as recited in claim 33, further comprising a trigger for actuating the spring injector mechanism and wherein the trigger is formed of stamped sheet metal.

44. The method as recited in claim 33, further comprising a trigger for actuating the spring injector mechanism and wherein the trigger is formed of stamped sheet steel.

45. The method as recited in claim 33, further comprising a trigger for actuating the spring injector mechanism and the trigger is formed in a stair-stepped configuration to eliminate a need for a pivot pin therefor.

46. The method as recited in claim 33, wherein the spring injector mechanism comprises:
a spring disposed within the housing;
a piston configured to be moved by the spring; and
a shaft configured to be moved by the piston.

47. The method as recited in claim 33, wherein the spring injector mechanism comprises:
a spring disposed within the housing;

a piston configured to be moved by the spring; and a glass reinforced polymer shaft configured to be moved by the piston.

48. The method as recited in claim 33, wherein the spring injector mechanism comprises:

a spring disposed within the housing;

a piston configured to be moved by the spring; and a shaft configured to be moved by the piston;

wherein the shaft is configured to inhibit grasping thereof so as to inhibit cocking of the spring injector mechanism.

49. The method as recited in claim 48, further comprising an ampule from which the shaft forces fluid when the shaft is moved.

50. The method as recited in claim 48, further comprising an ampule permanently attached to the housing.

51. The method as recited in claim 48, further comprising an ampule threadedly attached and adhesively bonded to the housing.

52. The method as recited in claim 48, further comprising an ampule threadedly attached and sonically welded to the housing.

53. The method as recited in claim 33, wherein the spring injector mechanism comprises a closed, but not ground, music wire helical spring.

54. The method as recited in claim 33, wherein the housing and the spring injection mechanism are configured to be disposable.

55. A needleless injector made according to the method comprising:

forming a housing from a non-metallic material;

placing a spring injector assembly at least partially within the housing;

and wherein the step of placing the spring injector assembly at least partially within the housing comprises:

placing a generally annular piston slidably upon a shaft, the shaft being slidable relative to the piston;

placing a helical compression spring slidable upon the piston; and placing the piston, shaft and the spring into the housing such that a portion of the shaft extends out of the housing for grasping by a user.

56. A needleless injector comprising:

spring means for forcing fluid from an ampule to perform an injection, the spring means comprising a shaft partially coaxially disposed within a piston;

housing means for containing the spring injector means; and wherein both the spring means and the housing means are useable only one time by making the spring means substantially incapable of resetting with a user's bare hand.

57. A method for performing an injection, the method comprising the steps of:

performing an injection step for forcing fluid from an ampule via a needleless spring injector, the needleless spring injector comprising a shaft partially coaxially disposed within a piston; and performing a disposal step for disposing essentially the entire needleless spring injector after only one use.

58. A needleless injector comprising:

a housing;

a spring disposed within the housing;

a piston configured to be moved by the spring; and a shaft configured to be moved by the piston;

wherein the shaft extends from a proximal end of the housing and out of the housing to facilitate filling an ampule disposed at a distal end of the housing by grasping on the portion of the shaft that extends out of the housing with a user's bare hand and moving the shaft relative to the piston.

59. The needleless injector as recited in claim 58, wherein the shaft extends from the distal end of the housing to facilitate ejection of fluid from an ampule.

60. A needleless unit dose injector comprising:

a housing;

a spring disposed within the housing;

a piston configured to be moved by the spring;

a shaft configured to be moved by the piston; and an ampule containing medication;

wherein a proximal portion of the shaft has been removed from a distal portion of the shaft after the proximal portion of the shaft has been used to cock the shaft to deter recocking.

61. A needleless injector assembly comprising a housing having a distal end, a proximal end, and a longitudinal exterior surface; an ampule attached to the distal end of the housing; a spring injector assembly disposed at least partially within the housing, the spring injector assembly comprising a shaft partially coaxially disposed within a piston and a spring coaxially disposed over at least a portion of the piston; a lever for engaging the piston to keep the spring injector assembly in a cocked position; a trigger having a squeezing surface positioned adjacent the longitudinal exterior surface of the housing adapted to move the lever which then releases the piston; and wherein the shaft comprises a proximal end in fluid communication with the ampule and a distal end that extends from the distal end of the housing.

62. The needleless injector assembly of claim 61, wherein the spring injector assembly is cocked by pulling on the distal end of the shaft that extends from the distal end of the housing so that the lever engages the piston.

63. A needleless injector assembly comprising a housing having a distal end and a proximal end, an ampule for containing a fluid attached to the distal end of the housing, a spring injector assembly comprising a shaft partially coaxially disposed within a piston and the piston coaxially disposed with a spring, wherein the shaft comprises a proximal end that extends from the proximal end of the housing, a distal end that is adapted to pass inside the ampule, and a shoulder disposed in between the proximal end and the distal end of the shaft, and wherein the piston comprises a piston head for pushing the shoulder; a lever for contacting with the piston head to maintain the spring injector assembly in a cocked positioned; and a trigger for squeezing, which when squeezed is adapted to remove the contact between the lever and the piston head to thereby permit the piston to be propelled by the spring.

64. The needleless injector assembly of claim 63, further comprising a safety mechanism for preventing the trigger from being squeezed when activated.

65. A method for delivering medication contained inside an injector assembly subcutaneously without a needle comprising the steps:

cocking a spring injector assembly disposed at least partially within a housing; the spring injector assembly comprising a piston comprising a piston head, a shaft coaxially disposed with the piston and having a proximal end, a distal end, and a shoulder disposed in between the proximal end and the distal end, and a spring coaxially disposed with the piston;

filling the injector assembly with medication by filling an ampule attached to a distal end of the housing with medication; and firing the spring injector assembly by placing the ampule next to a surface of a body and pulling on a trigger disposed on a side of the housing;

wherein the step of cocking the spring injector assembly comprises the step of pulling on the proximal end of the shaft to cause the shoulder to push against the piston head until a lever engages the piston head to maintain the spring injector assembly in the cocked position; and wherein the step of filling the injector assembly comprises the step of grasping on the proximal end of the shaft and moving the proximal end of the shaft from a first position to a second position after the piston has been cocked.

66. The method of claim 65, further comprising the step of disposing substantially all of the injector assembly after the firing step.

* * * * *